(12) United States Patent
Eisenschmid et al.

(10) Patent No.: US 7,362,105 B2
(45) Date of Patent: Apr. 22, 2008

(54) INTEGRATED MICROSTRUCTURE SENSOR ELEMENT FOR DETECTING THERMODYNAMIC VARIABLES OF A FLUID

(75) Inventors: Heinz Eisenschmid, Ditzingen-Hirschlanden (DE); Carsten Raudzis, Leinfelden-Echterdingen (DE); Michael Stumber, Korntal-Muenchingen (DE)

(73) Assignee: Robert Bosch GmbH, Stuttgart (DE)

( * ) Notice: Subject to any disclaimer, the term of this patent is extended or adjusted under 35 U.S.C. 154(b) by 776 days.

(21) Appl. No.: 10/150,425

(22) Filed: May 17, 2002

(65) Prior Publication Data

US 2003/0033861 A1 Feb. 20, 2003

(30) Foreign Application Priority Data

May 17, 2001 (DE) ................................. 101 23 920

(51) Int. Cl.
*G01N 27/60* (2006.01)
*G01N 25/00* (2006.01)
*G01N 25/18* (2006.01)

(52) U.S. Cl. ..................... 324/453; 324/451; 73/61.76; 374/44

(58) Field of Classification Search ................ 213/453, 213/451; 73/61.76; 374/43, 44, 152
See application file for complete search history.

(56) References Cited

U.S. PATENT DOCUMENTS 5,251,980 A * 10/1993 Hiraoka et al. ............... 374/44
5,439,291 A * 8/1995 Reading ....................... 374/43
5,667,301 A * 9/1997 Jurkowski et al. ............ 374/43
6,169,965 B1 * 1/2001 Kubisiak et al. ........... 73/61.76
6,535,824 B1 * 3/2003 Mansky et al. ............... 374/49

OTHER PUBLICATIONS

N.O. Birge et al., "Specific Heat Specroscopy: Origins, Status and Applications of the 3ω-Method", Thermochimica Acta, 304/305, pp. 51-66 (1997).

* cited by examiner

*Primary Examiner*—Andrew H. Hirshfeld
*Assistant Examiner*—Timothy J Dole
(74) *Attorney, Agent, or Firm*—Kenyon & Kenyon LLP

(57) ABSTRACT

An integrated microstructure sensor element is proposed for detecting thermodynamic measured variables of a fluid. To that end, a supporting body, particularly a board or a wafer having at least one microstructured heating element in contact with the fluid during operation, is provided, on which or in whose vicinity are arranged first arrangement for at least intermittently acting on the heating element with an electric alternating current of defined frequency or a defined frequency band, as well a second arrangement for detecting the amplitude of the third harmonic wave of the electric voltage applied to the heating element. The proposed microstructure sensor element in the form of a compact, integrated component is suitable in particular for determining or monitoring the thermal conductivity and/or the thermal capacity of a fluid, particularly an oil in a motor vehicle.

22 Claims, 2 Drawing Sheets

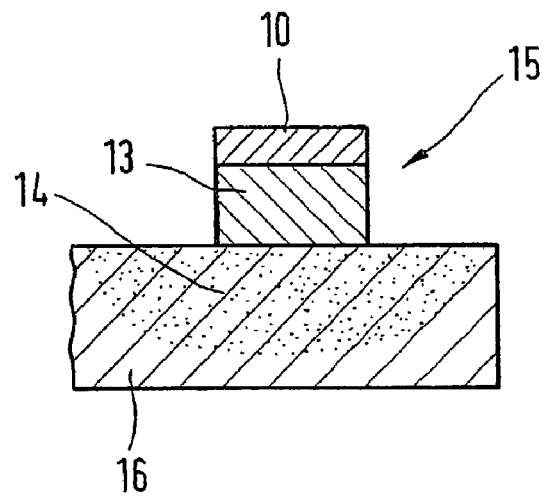
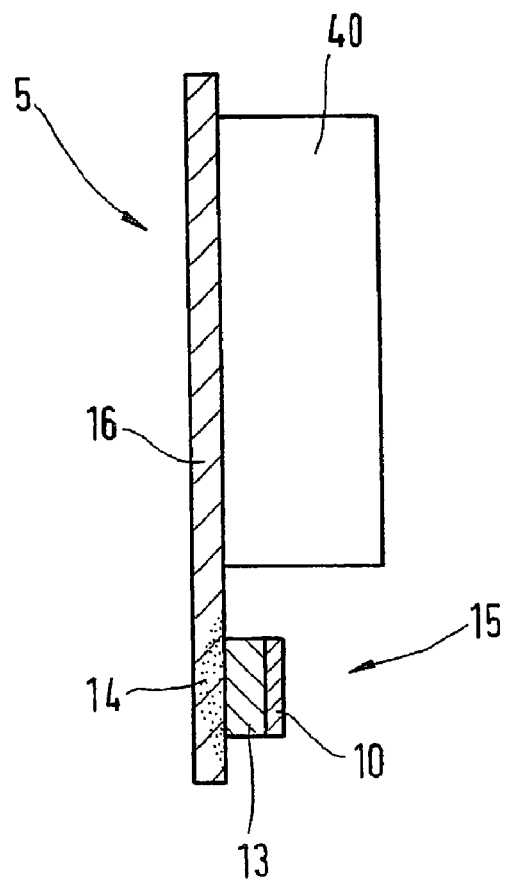

INTEGRATED MICROSTRUCTURE SENSOR ELEMENT FOR DETECTING THERMODYNAMIC VARIABLES OF A FLUID

FIELD OF THE INVENTION

The present invention relates to an integrated microstructure sensor element for detecting thermodynamic variables of a fluid, particularly for determining or monitoring the thermal conductivity and/or the thermal capacity of a fluid, for example, of an oil in a motor vehicle.

BACKGROUND INFORMATION

Determining thermodynamic variables of a fluid such as the thermal conductivity and the thermal capacity of a super-cooled liquid near the glass transition with the aid of the so-called 3ω method is described in N. O. Birge et al., "Specific Heat Spectroscopy: Origins, Status and Applications of the 3ω-Method", Thermochimica Acta, 304/305, (1997), pp. 51 through 66, in which the theoretical fundamentals of the 3ω method and the procedure for determining the thermal conductivity and the thermal capacity of a fluid with the aid of this method are also explained in detail.

Moreover, a sensor element is described there in which planar heating elements having an electroconductive nickel coating are provided on a borosilicate glass substrate and are dipped into a fluid. A periodic heating current is applied to this sensor element via external electrical components, and the third harmonic wave of the electric voltage applied to the heating element is evaluated.

However, this sensor element is a laboratory design which is not suitable for routinely determining thermodynamic variables of a fluid. In particular, this sensor is not sufficiently compact to, for example, incorporate it in a motor vehicle and use it there for monitoring the condition of the oil.

In principle, when working with the 3ω method, a thermal diffusion wave is produced by transient heating, amplitude and penetration depth of this wave being small, so that thermal conductivity $\lambda$ and thermal capacity $c_p$ may be determined in a substantially trouble-free manner, i.e. without significant temperature rise.

The object of the present invention is to provide a compact sensor element, able to be manufactured in series production, for continuously determining or monitoring the thermal capacity and/or the thermal conductivity of a fluid such as an oil in a motor vehicle.

SUMMARY OF THE INVENTION

The integrated microstructure sensor element of the present invention has the advantage that it makes it possible to determine both the specific thermal capacity and the thermal conductivity of a fluid such as an oil.

A further advantage compared to the related art is the simplified and, above all, considerably miniaturized and integrated design of the microstructure sensor element according to the present invention. Thus, according to the invention, a heating element, applied on a substrate whose heat-conducting properties are as poor as possible, is produced using customary thin-film technology and is utilized for carrying out the 3ω method, the heating element being inexpensive to produce and having a compact design.

A further advantage of the integrated microstructure sensor element according to the present invention is that it may easily be combined with sensor elements likewise able to be produced using microsystem technology or thin-film technology, so that if necessary, a plurality of measuring principles, i.e. a plurality of sensor elements, may be combined in a very compact manner in one housing, or on one chip or one board. Using this combination, in addition to the thermodynamic measured variables detected by the microstructure sensor element of the present invention, further measured variables such as electric conductivity, viscosity or impedance may be inexpensively acquired, as well.

With respect to a compact type of construction and a design which is as sturdy as possible and suitable for series production, it is particularly advantageous if the electronic components for acting upon the heating element with an electric alternating current of a defined frequency or a defined frequency band, or with electric alternating currents having a plurality of different defined frequencies or frequency bands in succession, as well as the electronic components for detecting the sensor signal are also arranged on or in the immediate vicinity of the supporting body on which the actual heating element is situated. This local proximity can be achieved by situating the electronic components on a first board or an evaluation/signal-IC, and situating the heating element on a second, adjacently positioned board or a chip or wafer, or disposing the electronic components and the heating element on a joint chip or IC. Advantageously achieved in each case is that the integrated microstructure sensor element of the present invention is able to be produced in one piece or two pieces as a complete sensor module, and may be installed in a simple manner in motor vehicles.

Thus, it is particularly advantageous if the heating element has a platinum printed circuit trace and/or a platinum conducting layer, which is electroconductively connected to the first arrangement and the further arrangement via connector contact faces. Platinum has particularly favorable electrical properties and is corrosion-stable. In has also turned out to be particularly advantageous if the platinum printed circuit trace or platinum conducting layer is in a meander form.

Incidentally, the heating element should be interconnected with the electronic components, cooperating with it, via metallic printed circuit traces in a known manner such that no additional contact resistances interfering with the sensor signal develop.

If the intention is to cover a broad spectrum of frequencies of the electric alternating current applied to the heating element, it is advantageous if a plurality of heating elements is provided having different thickness and, above all, variable width of the platinum printed circuit trace or conducting layer.

To achieve the best possible thermal isolation of the actual printed circuit trace or conducting layer of the heating element from the supporting body, it is advantageous if the heating element is arranged on a material having the poorest possible thermal conductivity, particularly on a supporting-body region exhibiting poor heat conductivity. To that end, the supporting body, at least in the region of the heating element, is preferably made of a material exhibiting poor thermal conductivity such as glass, particularly borosilicate glass, or an amorphous material.

It has proven to be particularly advantageous if the supporting body, at least in the region of the heating element, is made of silicon; a silicon oxide layer or, particularly advantageous, a layer or a region of porous silicon is provided as a supporting-body region having poor heat conductivity between the heating element and the silicon.

To achieve the best possible thermal isolation of the heating element from the supporting body, a further advantageous refinement of the integrated microstructure sensor element provides for arranging the heating element on an at least substantially self-supporting film, a web or a membrane which has been patterned out of the supporting body or produced on it in a manner known per se. Such a film, web or membrane makes it possible to achieve a particularly compact, integrated type of construction compatible with customary manufacturing processes of silicon surface micromechanics.

BRIEF DESCRIPTION OF THE DRAWINGS

FIG. 3 is a sectional view through the heating element according to FIG. 1.

FIG. 4 is a sectional side view of the microstructure sensor element according to FIG. 1.

DETAILED DESCRIPTION

Figure 1:
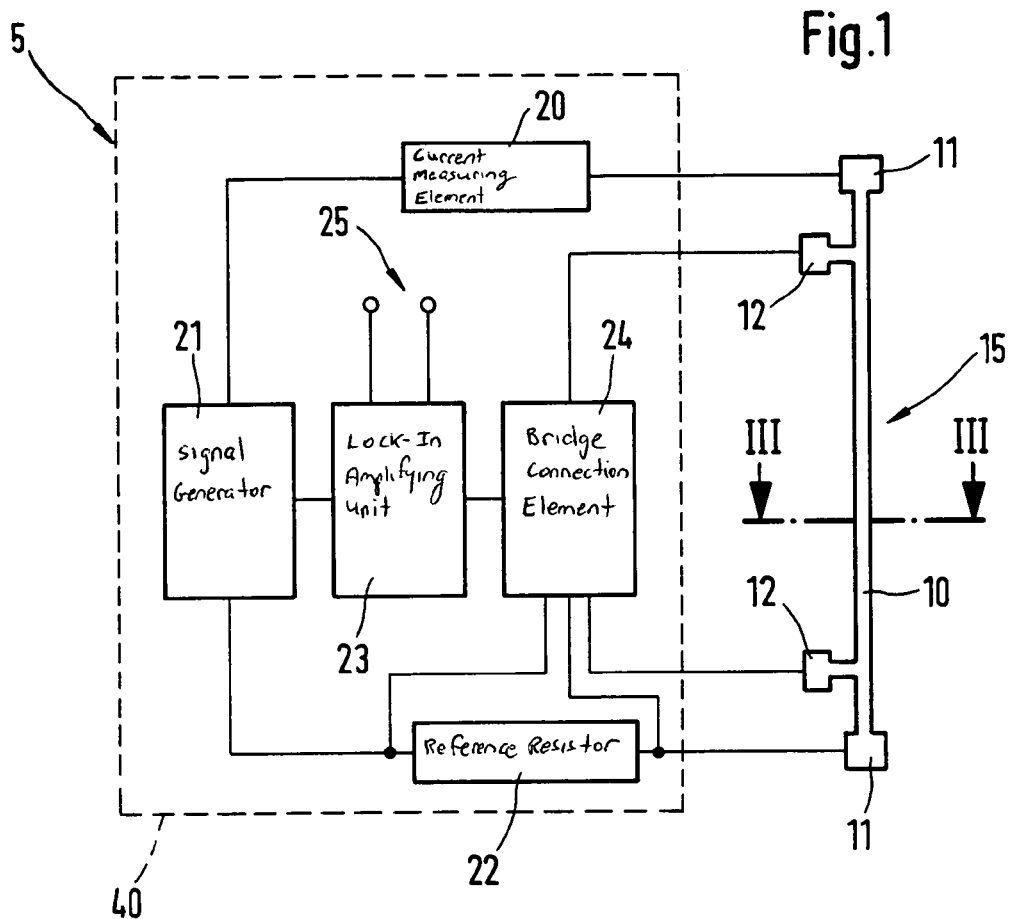
FIG. 1 is a plan view of an integrated microstructure sensor element on a substrate having a strip-shaped heating element and electronic subassemblies.

The invention starts out initially from the known $3\omega$ method for determining the thermal conductivity and the thermal capacity of a fluid, as is described in detail in N. O. Birge et al, Thermochimica Acta, 304/305, (1997), pp. 51 through 66. In the example explained, this method is used for monitoring the oil of a motor vehicle during its operation, and is implemented using integrated microstructure sensor element 5 clarified in the following.

This microstructure sensor element 5, as altogether a sensor module, provides an output signal which is supplied to an evaluation unit (not shown), integrated into the motor vehicle, which determines from it the desired thermodynamic variables, as explained in the cited document, and transmits the results to the engine management of the motor vehicle and/or to a driver information system.

In principle, to that end, according to the $3\omega$ method, a periodic heating current having a defined frequency or a sequence of defined frequencies is first of all impressed on a heating element 15 of integrated microstructure sensor element 5, and the third harmonic wave of the electric voltage applied in each case to heating element 15 is detected using a lock-in amplifying element 23. Thermal capacity $c_p$ and thermal conductivity $\lambda$ of the fluid to be monitored, which is in contact with heating element 15, may then be determined from the amplitude of this third harmonic wave. As a rule, alternating currents of different, definitively predefined frequency act upon heating element 15 in succession, so that a plurality of measuring points is obtained, for example, at 100 Hz, 500 Hz, 2 kHz, 4 kHz and 10 kHz.

In this connection, care should be taken that a conducting layer 10 of heating element 15 conducting the electric alternating current exhibits a highest possible temperature coefficient, and is thermally isolated as well as possible with respect to a supporting body 16 situated under it, so that the electric alternating current applied to heating element 15 essentially causes a heating of the fluid to be monitored, and not a temperature rise in supporting body 16 which would invalidate the measuring result.

In detail, FIG. 1 shows an integrated microstructure sensor element 5, which is constructed on a supporting body 16. This supporting body 16, at least in the region of actual heating element 15, exhibits poor thermal conductivity, and is implemented there, for example, as a borosilicate glass substrate.

Heating element 15 is structured in the form of a strip which, at each of its two ends, has first connector contact faces 11 and second connector contact faces 12. As can be seen from FIG. 3, which shows heating element 15 according to FIG. 1 in section, it is composed of a conducting layer 10 which is set apart from supporting body 16 by an intermediate layer 13.

Intermediate layer 13 is used to improve the adhesion of conducting layer 10 on supporting body 16, as well as to thermally isolate conducting layer 10 with respect to the supporting body. To that end, it is implemented, for example, as a chromium layer having a thickness of a few nanometers.

In the exemplary embodiment explained, actual conducting layer 10 is a platinum layer which has been structured in a known manner as a strip-shaped printed circuit trace. It has a width of 2 µm to 500 µm, particularly 2 µm to 100 µm, and a thickness of 20 nm to 5 µm, particularly 20 nm to 500 nm. During operation of microstructure sensor element 5, it is in contact with the fluid to be monitored and/or analyzed.

FIG. 1 also shows how further electronic subassemblies are disposed on supporting body 16 in a surrounding area of heating element 15.

Going into detail, a signal generator 21 is provided with which an electric alternating current is generated having amplitude and frequency predefinable, for example, via a microprocessor of the evaluation unit (not shown). The electric alternating current is preferably a sinusoidal alternating current, that is to say, signal generator 21 is a sine-wave generator which generates the sinusoidal alternating current having a frequency between 0.1 Hz and 20 kHz, particularly between 100 Hz and 10 kHz, and an amplitude between 1 mA and 1 A, particularly between 1 mA and 200 mA.

Furthermore, according to FIG. 1, the electric alternating current generated by signal generator 21 is supplied to first connector contact faces 11, so that a periodic electric alternating current of defined frequency, which heats the fluid to be analyzed or monitored, is applied to heating element 15.

Alternatively to a sinusoidal alternating current, an alternating current having a defined frequency band may also be used, this frequency band preferably being as narrow as possible.

For monitoring or also for adjusting the amplitude of the electric alternating current generated by signal generator 21, according to FIG. 1, an optional current measuring element 20 is provided whose function may also be integrated into signal generator 21. Moreover, FIG. 1 shows that interposed between signal generator 21 and one of first connector contact faces 11 is a reference resistor 22 at which a defined voltage drops. Suitable integrated electronic components for implementing a current measuring element 20, a reference resistor 22 and signal generators 21 are sufficiently known from the related art, or are available as integrated circuits for mounting on a board.

Also provided in FIG. 1 is a lock-in amplifying element 23 whose reference input is connected to a second output of signal generator 21, so that the output signal of signal generator 21 supplied to heating element 15, however trebled with respect to the frequency, is also available to lock-in amplifying element 23 as reference. Alternatively, however, besides the direct provision of this output signal, trebled in frequency, by signal generator 21 explained, an additional electronic component may also be provided which is connected between signal generator 21 and lock-in amplifying element 23 and carries out such a trebling of frequency.

The second input of lock-in amplifying element 23 is connected to second connector contact faces 12 via a bridge connection element 24. Bridge connection element 24 is implemented in the form of a Wheatstone bridge connection, as is described in N. O. Birge et al., Thermochimica Acta, 304/305, pp. 51 through 66.

Going into detail, bridge connection element 24 is connected to both second connector contact faces 12, so that the electric voltage applied between second connector contact faces 12 is supplied to bridge connection element 24. Furthermore, the electric voltage dropping at reference resistor 22 is supplied as reference voltage to bridge connection element 24. The output signal of bridge connection element 24 is finally available as input signal at lock-in amplifying element 23.

Lock-in amplifying element 23 is designed in such a way that it is thereby possible to detect the third harmonic wave of the electric voltage applied to heating element 15 between second connector contact faces 12.

The amplitude of the third harmonic wave is finally made available at output 25 of lock-in amplifying element 23 in amplified form as output signal and is supplied to an evaluation unit (not shown) where it is further processed for determining the thermal conductivity and/or the thermal capacity of the fluid with which heating element 15 is in contact.

Figure 2:
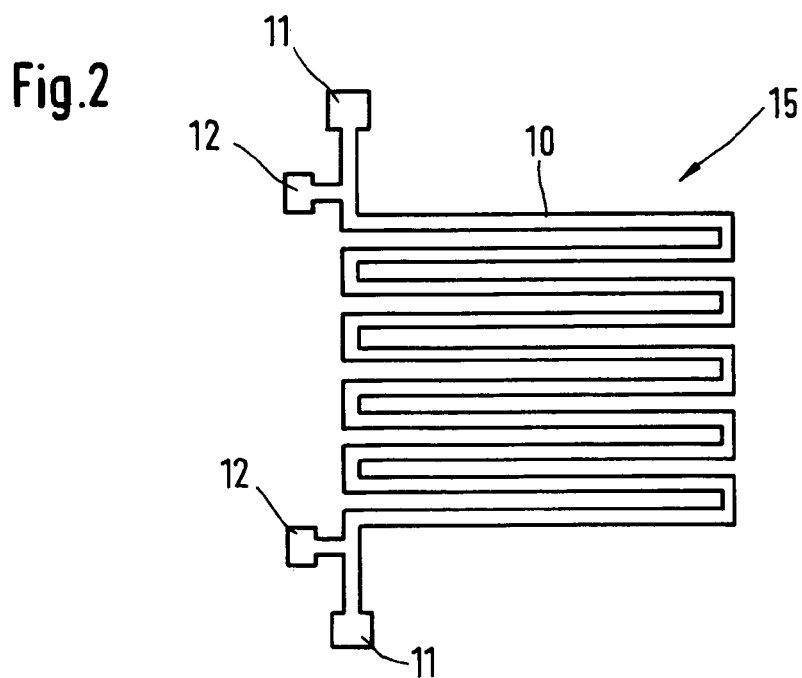
FIG. 2 illustrates an alternative specific embodiment of the heating element according to FIG. 1.

FIG. 2, in a plan view, clarifies an alternative specific embodiment of heating element 15 which, in contrast to strip-shaped heating element 15 according to FIG. 1, is now meander-shaped and covers a rectangular area. Apart from that, heating element 15 according to FIG. 2 corresponds in its design to heating element 15 according to FIG. 1.

FIG. 3 shows heating element 15 according to FIG. 1 in section, in this case, supporting body 16 below heating element 15 being in the form of a supporting-body region 14 made of porous silicon. For that purpose, initially used as supporting body 16 in this region was a silicon wafer which was then made porous in a known manner in supporting-body region 14. Porous silicon exhibits a perceptibly reduced thermal conductivity compared to silicon, so that good thermal isolation of heating element 15 with respect to supporting body 16 is thereby achieved.

Finally, FIG. 4 shows a side view of integrated microstructure sensor element 5 according to FIG. 1, electronic subassemblies 20, 21, 22, 23, 24 according to FIG. 1 being covered by a cap 40 which provides protection from outside influences, e.g. the fluid.

Incidentally, integrated microstructure sensor element 5 explained may also have a plurality of heating elements 15 having different thickness and/or different width of conducting layer 10, these different heating elements 15 then in each case covering different frequency ranges. In this way, the desired thermodynamic measured variables of the fluid are determinable over a particularly large frequency range.

To thermally isolate heating element 15 with respect to supporting body 16, as explained, supporting body 16, at least in the region in which the heating element is positioned, may be constructed of glass, e.g. borosilicate glass, or an amorphous material exhibiting poor heat conductivity. Alternatively, however, supporting body 16 may also be constructed from silicon, for example, in the form of a chip or a wafer, a supporting-body region 14 having poor heat-conducting properties which, as already explained, is made of porous silicon or silicon oxide, then being provided between heating element 15 and the silicon.

A further specific embodiment of integrated microstructure sensor element 5 provides for the thermal isolation of heating element 15, by arranging it on an at least substantially self-supporting film, web or a membrane.

With respect to further particulars regarding the 3ω method and the evaluation process for determining the thermodynamic measured variables of the fluid with the aid of integrated microstructure sensor element 5, reference is again made to N. O. Birge et al., Thermochimica Acta, 304/305, (1997), pp. 51 through 66.

What is claimed is:

1. An integrated microstructure sensor element for detecting thermodynamic measured variables of a fluid, comprising:
    a supporting body including at least one microstructured heating element in contact with the fluid during operation, the supporting body being a unitary body including a supporting body portion and a remainder portion integral with the supporting body portion, the supporting body portion having a poor thermal conductivity relative to the remainder portion and the fluid;
    a first arrangement situated one of on and in a vicinity of the supporting body, to at least intermittently act on the at least one microstructured heating element with an electric alternating current having one of a defined frequency and a defined frequency band; and
    a second arrangement to detect an amplitude of a third harmonic wave of an electric voltage applied to the at least one microstructured heating element.

2. The integrated microstructure sensor element according to claim 1, wherein the supporting body includes one of a printed circuit board and a wafer.

3. The integrated microstructure sensor element according to claim 1, wherein:
    the at least one microstructured heating element includes one of a platinum printed circuit trace and a platinum conducting layer having one of a strip-shape and a meander-shape, the heating element being electroconductively connected to the first arrangement and the second arrangement via connector contact faces.

4. The integrated microstructure sensor element according to claim 3, wherein:
    the at least one micro structured heating element includes a plurality of heating elements, one of the platinum printed circuit trace and the platinum conducting layer being different with respect to at least of a thickness and a width.

5. The integrated microstructure sensor element according to claim 1, wherein:
    the supporting body portion having poor thermal conductivity is made of glass.

6. The integrated microstructure sensor element according to claim 5, wherein:
    the glass includes at least one of borosilicate glass and an amorphous material.

7. The integrated microstructure sensor element according to claim 1, wherein:
    the supporting body is made from silicon and the supporting body portion being more porous than the remainder portion.

8. The integrated microstructure sensor element according to claim 1, further including:
    one of an at least substantially self-supporting film, an at least substantially self-supporting web, and an at least substantially self-supporting membrane between the supporting body portion and the at least one microstructured heating element.

9. The integrated microstructure sensor element according to claim 1, further including:
a material of a poor thermal conductivity between the at least one microstructured heating element and the supporting body, the material adapted to thermally isolate the microstructured heating element from the supporting body.

10. The integrated microstructure sensor element according to claim 9, wherein:
the material improves adhesion between the supporting body and the microstructured heating element.

11. The integrated microstructure sensor element according to claim 1, wherein:
the first arrangement includes a signal generator arranged on the supporting body.

12. The integrated microstructure sensor element according to claim 11, wherein:
the signal generator includes a sine-wave generator.

13. The integrated microstructure sensor element according to claim 11, wherein:
at least one of the following:
the signal generator is operable to generate the electric alternating current with one of pre-determinable and defined amplitude, and
the first arrangement includes a current measuring element for one of determining and stipulating the amplitude of the electric alternating current.

14. The integrated microstructure sensor element according to claim 11, wherein:
a bridge connection element is acted upon, via connector contact faces at the at least one microstructured heating element, with the electric voltage to be detected and an electric voltage dropping at a reference resistor, the bridge connection element being connected to a lock-in amplifying element, to which an output signal of the signal generator, trebled with respect to the defined frequency, is supplied at the same time as a reference signal.

15. The integrated microstructure sensor element according to claim 11, wherein:
the signal generator is operable to produce a sinusoidal alternating current having a frequency of 0.1 Hz to 20 kHz and an amplitude of 1 mA to 1 A.

16. The integrated microstructure sensor element according to claim 15, wherein:
the frequency of the sinusoidal alternating current is 100 Hz to 20 kHz and the amplitude thereof is 1 mA to 200 mA.

17. The integrated micro structure sensor element according to claim 1, wherein:
the second arrangement includes a lock-in amplifying element arranged on the supporting body for detecting the amplitude and a phase of the third harmonic wave.

18. The integrated microstructure sensor element according to claim 17, further comprising:
an evaluation unit connected to an output of the lock-in amplifying element, one of a thermal conductivity and a thermal capacity of the fluid being one of determined and monitored as a function of time using the output signal of the lock-in amplifying element.

19. The integrated microstructure sensor element according to claim 1, wherein:
the second arrangement includes a reference resistor and a bridge connection element arranged on the supporting body and interconnected according to a Wheatstone bridge.

20. The integrated microstructure sensor element according to claim 1, wherein:
one of a printed circuit trace and a conducting layer of the at least one microstructured heating element has a width of 2 μm to 500 μm and a thickness of 20 nm to 5 μm.

21. The integrated microstructure sensor element according to claim 20, wherein:
the width is 2 μm to 100 μm and the thickness is 20 nm to 500 nm.

22. A method for detecting thermodynamic measured variables of a fluid using an integrated microstructure sensor element comprising a supporting body including at least one microstructured heating element, the supporting body made of a unitary body including a supporting body portion and a remainder portion integral with the supporting body portion, the supporting body portion having a low thermally conductivity relative to the remainder portion and the fluid, comprising:
a) thermally isolating the heating element from the remainder portion by placing the heating element over the supporting body portion such that the supporting body portion lies between the heating element and the remainder portion;
b) contacting the heating element with the fluid;
c) while maintaining contact between the heating element and the fluid operating a first arrangement to at least intermittently act on the at least one heating element with an electric alternating current having one of a defined frequency and a defined frequency band, said first arrangement being one of on and in a vicinity of the supporting body; and
d) detecting an amplitude of a third harmonic wave of an electric voltage applied to the at least one heating element.

* * * * *